United States Patent [19]

Teotino et al.

[11] 3,954,777

[45] *May 4, 1976

[54] AMINOPROPIONYL DERIVATIVES OF 2,3-DIPHENYL CYCLOPROPYLAMINE

[75] Inventors: Uberto Teotino; Davide Della Bella, both of Milan; Dario Chiarino, Monza (Milan), all of Italy

[73] Assignee: Zambon S.p.A., Milan, Italy

[ * ] Notice: The portion of the term of this patent subsequent to May 4, 1993, has been disclaimed.

[22] Filed: Feb. 26, 1971

[21] Appl. No.: 119,347

[30] Foreign Application Priority Data
Mar. 3, 1970    Italy.................................. 21403/70

[52] U.S. Cl..................... 260/293.76; 260/326.43; 260/562 N; 260/562 B; 424/267; 424/274; 424/324

[51] Int. Cl.²..................................... C07D 295/14

[58] Field of Search........ 260/293.76, 326.5, 562 N, 260/562 B, 326.43

[56] References Cited
UNITED STATES PATENTS 3,192,229   6/1965   Biel................................. 260/326.5
3,562,276   2/1971   Teotino et al...................... 260/268

*Primary Examiner*—G. Thomas Todd
*Attorney, Agent, or Firm*—Stevens, Davis, Miller & Mosher

[57]    ABSTRACT

New aminopropionyl derivatives of 2,3-diphenylcyclopropylamine of the formula

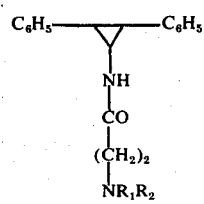

wherein $R_1$ is H or lower alkyl; $R_2$ is H, lower alkyl, benzyl or together with $R_1$ and the nitrogen atom to which they are bound is a heterocyclic ring as well as their non toxic addition salts with organic and inorganic acids. The new compounds are endowed with anticonvulsant and anti-cardiac arrhythmias activity.

3 Claims, No Drawings

AMINOPROPIONYL DERIVATIVES OF 2,3-DIPHENYL CYCLOPROPYLAMINE

The present invention is concerned with new aminopropionyl derivatives of 2,3-diphenylcyclopropylamine, the process for their preparation and pharmaceutical compositions containing them.

More precisely the invention is concerned with compounds of the formula

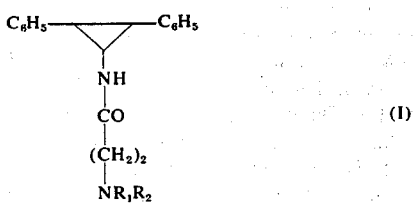

wherein $R_1$ is H or lower alkyl $R_2$ is H, lower alkyl, benzyl or together with $R_1$ and the nitrogen atom to which they are bound, is an heterocyclic ring, as well as with their non toxic acid addition salts with organic or inorganic acids.

The present invention is further concerned with the compounds of formula

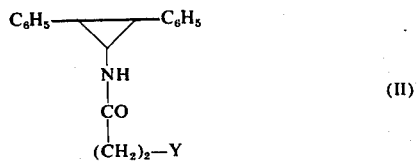

wherein Y is a halogen atom, which are the intermediate, compounds for the preparation of compounds of formula (I).

The new compounds of the invention may exist as cis-cis, cistrans and trans-trans geometrical isomers, besides d, l and d,l optical isomers.

When no different indication is given in the course of the present description, it is intended that we refer both to each geometrical or optical isomer and to mixtures thereof and also that all said isomers are protected by the present patent.

The process adopted to prepare the new compounds of the present invention may be represented by the following scheme:

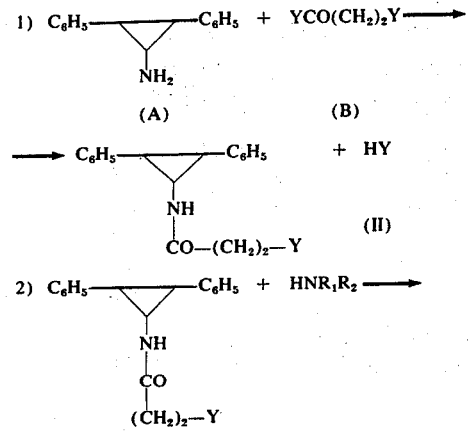

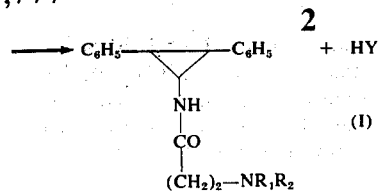

wherein Y, $R_1$ and $R_2$ have the above given meaning.

The step (1) of the process is carried out by reacting the compound (A) or an acid addition salt thereof with the compound (B) in the presence of an acid binding substance and of an inert solvent or mixture of inert solvents at a temperature preferably comprised between 0° and 50°C. The preferred method is that according to Schotten-Baumann. The step (2) is carried out by reacting the compound of formula (II) with an amine of formula $NHR_1R_2$, wherein $R_1$ and $R_2$ have the above given meaning, in the presence of an inert solvent or mixture of inert solvents and of an acid binding substance, at a temperature comprised between 50° and 200°C. Preferably an excess of the same amine is used both as acid binding substance and as solvent. If the amine is a low-boiling one the reaction is carried out in a sealed tube while if the amine has a high-boiling point is is preferred to operate at the boiling temperature of the reaction mixture. The obtained products are therapeutically useful as anticonvulsivants and anti-cardiac arrythmias drugs. The anticonvulsivant activity has been pointed out through the tests of crisis produced with electroshock or with cardiazol. Materials and methods. The animals used in the tests, unless otherwise indicated, were male albine Swiss mice weighing 19–23 g; each animal has been used only once. The compounds have been injected as hydrochlorides under skin (0.1 ml/10 g) 30 minutes ante; in order to determine the $LD_{50}$, the administration has been performed intraperitoneally and the deaths have been counted within the 72 Hours following the treatment.

As reference compounds there have been used: ethosuximide under skin, 30 minutes ante; phenurone per os 60 minutes ante; phenobarbital sodium salt under skin 30 minutes ante; phenitoine sodium salt under skin 30 minutes ante; trimethadione under skin 30 minutes ante; primidone per os 6 hours ante and mephenesin under skin 30 minutes ante. Electroshock (M.E.S.). The method followed in performing the electroshock is C. H. Cashin and J. Jackson's method (J.Pharm.Pharmacol.,1962, 14 (supl.) 445) modified as follows: the electrodes are placed in the outer ear which is, before the shock, filled with a physiological solution. The applied voltage is of 92 volts with a current of 50 Hz stabilized with Selonix H.T. 4420 stabilizer; duration of shock 0.2 seconds. The animals are considered as protected when the extensor phase of the hind paws does not appear during the tonic crisis. Under such conditions the results obtained with the reference compounds are in good agreement with those reported in the art for the same compounds. (E. A. Swinyard, W. C. Brown; L. S. Goodman, J. Pharmacol., 1952, 106, 319) Schock by cardiazol (M.M.S.). 38 mg/kg of cardiazol, under the form of a 0.38% aqueous solution, is quickly injected in the dorsal vein of the mouse tail (L. S. Goodman, M. Singh Grewal, W. C. Brown, E. A. Swinyard, J. Pharmacol. 1953, 108, 168). The animals are considered as protected when the extensor phase of the hind paws is eliminated during the tonic crisis. The so obtained data have been elaborated by calculating the $ED_{50}$ and the $LD_{50}$ according to Lichtfield-Wilcoxon's method (J. Pharmacol. 1949, 96, 99). The $ED_{50}$ and $LD_{50}$ values of the reference compounds have been reported in Table 1, while those of the new compounds according to the present invention are reported in Table 2.

TABLE 1

| Reference compounds | M.E.S.-$ED_{50}$ mg/kg | M.M.S. $ED_{50}$ mg/kg | $LD_{50}$ mg/kg |
|---|---|---|---|
| Phenurone (1,1-dimethyl-3-phenyl-urea) | 115 (92–132) | 50 (33–75) | |
| Phenobarbital sodium salt | 35 (27.5–46) | 4.5 (2.9–6.9) | 182 |
| phenitoine sodium salt | 15 (12.9–17.7) | 7.1 (5.6–8.8) | 120 |
| Trimethadione | | 175 (148.3–206.5) | |
| primidone | | 5.2 (3.4–7.8) | |
| ethosuximide | | 50 (36.4–68.5) | |
| mephenesin | 245 (196–307) | 180 (165.1–196.2) | |

TABLE 2

| Configuration | Formula $R_1$ | $R_2$ | $ED_{50}$ mg/kg M.E.S. | M.M.S. | $LD_{50}$ mg/kg |
|---|---|---|---|---|---|
| cis-trans | H | $CH_3$ | >120 | >120 | 120 (112–127) |
| cis-trans | H | $C_2H_5$ | >90 | >90 | 89.5 (78.5–102) |
| cis-trans | $CH_3$ | $CH_3$ | 21.8 (18.2–26.2) | 16.5 (14.4–18.8) | 88 + (77.1–100.3) |
| cis-trans | $C_2H_5$ | $C_2H_5$ | 33.5 (30–37.5) | 27 (23.7–31.8) | 79 (69.9–89.2) |
| cis-trans | $CH_3$ | $CH_2$—$C_6H_5$ | 91 (67–124) | 98 (75.3–127.4) | |
| cis-trans |  | | 24 (18.9–30.5) | 20 (17.2–23.3) | |
| cis-trans |  | | 16 (13.9–18.4) | 15 (13.6–16.5) | |
| cis-trans |  | | 275 (185–413) | | |

+ The compound has been administered as a 2% suspension in gum-arabic

As it is evident from the reported data, it has been surprisingly found that the anticonvulsant activity of the new compounds according to the invention is very good and even very often higher than that of the best among the known compounds presently on the market, when both the hydrogen atoms of the terminal amine group are substituted with lower alkyls and when the nitrogen atom of said amine group is part of an heterocyclic ring.

Moreover it has been found that the anticonvulsant activity is stronger for the cis-trans than for the trans-trans compounds, so that the former ones are a particular object of the present invention. The new compounds of the invention are deprived of MAO-inhibiting activity in live rats, both on the mithocondres of hepatic tissue and on the mithocondres and homogenatous of cerebral tissues, even if administered in doses of 100–200 mg/kg per os. The new compounds of the present invention, as already found with the other anticonvulsive drugs, are endowed with good activity in cardiac arrythmias. The pharmacological results have been confirmed in clinical tests. The hereinafter reported examples have the purpose of illustrating the process for the preparation of the new compounds of the invention, without however limiting the same.

EXAMPLE 1

N-(beta-chloro)propionyl-2.3-cis,trans-diphenyl cyclopropylamine. A mixture consisting of 25 g (120 mM) of 2.3-cis,trans-diphenylcyclopropylamine dissolved in 150 ml of water, 800 ml of chloroform and 120 ml of N HCL, kept under stirring and at a temperature equal to or lower than +5°C, is added drop by drop and contemporaneously with a solution containing 15.25 g (120 mM) or chloropropionyl chloride in 150 ml of chloroform and with 10 g of NaOH dissolved in 150 ml of water. During the addition the pH is kept constantly alkaline. When the addition is completed the cooling bath is removed and stirring is continued for further 30 minutes. The organic phase is separated and washed first with 10% hydrochloric acid and then in succession with water, 10% aqueous solution of sodium bicarbonate and again with water. The organic extracts, dried on anhydrous sodium sulphate, are concentrated to dryness. The residue is pulped with petrol ether, filtered, dried at 50°C in air and crystallized from ethyl acetate. Yield 28.4 g; M.P. 145°–147°C In a similar manner also the N-beta bromopropionyl-2,3-cis,trans-diphenyl-cyclopropylamine (M.P. 150°–152°C from ethanol) is prepared.

EXAMPLE 2

N-(beta-methylamino)-propionyl-2,3-cis,trans-diphenyl cyclopropylamine hydrochloride. A mixture consisting of 10 g (33mM) of N-chloropropionyl-2,3-cis,trans-diphenylcyclopropylamine and 130 ml of a 25% solution of methylamine in ethanol (620 mM) is warmed in a sealed tube at 120°C over 24 hours. When the reaction is completed the mixture is cooled and the solvent and the unreacted amine are evaporated. The residue is taken up with water and acidified with hydrochloric acid at Congo Red. The resulting, turbid solution is washed by shaking it with ether, is decolorized with coal and filtered. The filrate is alkalized by adding potassium carbonate nearly up to saturation. The oily layer is extracted with chlorophorm and while the oily residue is discarded the chlorophorm extract is washed with water and dried on anhydrous sodium sulphate. The solvent is evaporated, the residue is dissolved in anhydrous ethyl ether and the solution is acidified at Congo Red with an ether solution of hydrochloric acid. The precipitate is filtered and dried at 50°C under vacuum. 10.20 g of product are obtained which is purified by crystallization from ethanol; M.P. 175°–177°C. In a similar manner the following products are prepared:

-N-(beta-ethylamino)propionyl-2,3-cis,trans-diphenylcyclopropylamine hydrochloride - M.P. 158°–160°C from ethanol -N-(beta-dimethylamino)-propionyl-2,3-cis,trans-diphenylcyclopropylamine M.P. 75°–76°C from hexane. -N-(beta-diethylamino)-propionyl-2,3-cis,trans-diphenylcyclopropylamine M.P. 52°–53°C from hexane -N-[beta-(N'-benzyl)methylamino]propionyl-2,3-cis,trans-diphenylcyclopropylamine hydrochloride. M.P. 203°–205°C from ethanol.

EXAMPLE 3

N-(beta-piperidine)propionyl-2,3-cis,trans-diphenyl-cyclopropylamine hydrochloride. 7 g (23.5 mM) of N-beta-chloro propionyl-2,3-cis,trans-diphenyl-cyclopropylamine are added little by little under stirring, at room temperature to 20 ml of piperidine. The mixture is refluxed over 12 hours. The excess piperidine is distilled off, the residue taken up with water and acidified at Congo Red with 10% hydrocloric acid. The turbid solution so obtained is washed by shaking it with ether, is decolourized with coal and filtered. The filtrate is alcalinized with 10% NaOH and extracted many times with chloroform. The various chloroform extracted fractions are washed with water and dried on anhydrous sodium sulphate. The chloroform is evaporated and the residue ( 13 g) is purified by crystallization from isopropylether; M.P. 99–101°C. In order to prepare the hydrochloride, the base is dissolved in ethanol at 60°C and acidified with ethanolic hydrochloric acid at Congo Red. It is filtered and added with an amount of isopropyl ether sufficient to crystallize out the hydrochloride; M.P. 185°–187°C. In a similar manner the following compounds are prepared:

-N-(beta-pyrrolidino)-propionyl-2,3-cis,trans-diphenylcyclopropylamine; M.P. 102°–104°C from isopropylether. -N-[beta-(4'-methyl)piperazino]-propionyl-2,3-cis,trans-diphenylcyclopropylamine; M.P. 93°–95°C from isopropyl ether. -N-[beta-(4'-methyl)piperazino]propionyl-2,3-cis,trans-diphenylcyclopropylamine hydrochloride; M.P. 218°–220°C from ethanol.

We claim:
1. A compound of formula

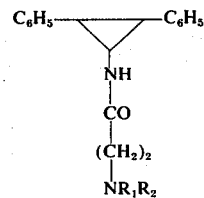

wherein $R_1$ is H or lower alkyl,
$R_2$ is H, lower alkyl, benzyl or together with $R_1$ and the
nitrogen atom to which they are bound, is pyrrolidino or piperidino as well as the non-toxic salts thereof with organic and inorganic acids.
2. A compound according to claim 1 having the cis-trans configuration.
3. A compound of the general formula

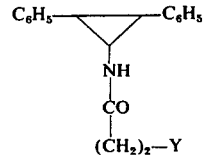

wherein Y is a halogen atom.

* * * * *